(12) United States Patent
Yiu

(10) Patent No.: US 6,464,943 B1
(45) Date of Patent: Oct. 15, 2002

(54) SOLID PHASE EVAPORATOR DEVICE

(76) Inventor: Felix H. Yiu, 17234 Bullock St., Encino, CA (US) 91316

( * ) Notice: Subject to any disclaimer, the term of this patent is extended or adjusted under 35 U.S.C. 154(b) by 0 days.

(21) Appl. No.: 09/391,271

(22) Filed: Sep. 7, 1999

(51) Int. Cl.[7] .............................. B01L 3/02; B01L 3/00; G01N 1/10; B01D 1/14; B01D 1/06; B01D 1/00

(52) U.S. Cl. ..................... 422/100; 422/99; 436/180; 159/22.1; 159/27.2; 159/27.4; 159/27.5; 159/28.5; 159/DIG. 41; 159/16.1

(58) Field of Search ................ 422/99, 100; 159/27.1, 159/27.2, 27.4, 27.5, 28.52, DIG. 41, 10.1; 203/DIG. 2

(56) References Cited

U.S. PATENT DOCUMENTS

| | | | |
|---|---|---|---|
| 1,204,300 A | | 2/1916 | Moore ..................... 159/13.2 |
| 3,568,735 A | * | 3/1971 | Lancaster ................. 141/238 |
| 3,650,306 A | * | 3/1972 | Lancaster ................. 141/238 |
| 3,977,935 A | | 8/1976 | Kowarski ................... 159/23 |
| 4,461,328 A | * | 7/1984 | Kenney |
| 4,465,554 A | | 8/1984 | Glass ........................ 159/16 |
| 4,554,839 A | * | 11/1985 | Hewett et al. ............ 73/864.16 |
| 4,642,220 A | | 2/1987 | Björkman .................. 422/101 |
| 4,704,255 A | | 11/1987 | Jolley ....................... 422/101 |
| 4,707,452 A | | 11/1987 | Friswell .................... 436/177 |
| 4,859,419 A | * | 8/1989 | Marks et al. ................ 422/56 |
| 4,952,518 A | * | 8/1990 | Johnson et al. ............ 436/518 |
| 5,005,981 A | | 4/1991 | Schulte et al. ............. 366/219 |
| 5,039,614 A | | 8/1991 | Dekmezian et al. .......... 436/43 |
| 5,100,623 A | | 3/1992 | Friswell .................... 422/68.1 |
| 5,108,603 A | | 4/1992 | Schuette ................ 210/321.72 |
| 5,151,154 A | | 9/1992 | Huercanos ................. 159/13.2 |
| 5,250,151 A | | 10/1993 | Huercanos ................. 159/47.1 |
| 5,260,028 A | | 11/1993 | Astle ......................... 422/81 |
| 5,283,039 A | | 2/1994 | Aysta ....................... 422/104 |
| 5,306,510 A | * | 4/1994 | Meltzer ...................... 422/65 |
| 5,514,336 A | | 5/1996 | Fox ........................... 422/64 |
| 5,525,302 A | * | 6/1996 | Astle ........................ 422/100 |
| 5,560,330 A | | 10/1996 | Andress et al. ........ 123/184.53 |
| 5,569,357 A | | 10/1996 | Kuhn et al. ................ 159/16.1 |
| 5,585,068 A | | 12/1996 | Panetz et al. ................ 422/64 |
| 5,598,933 A | | 2/1997 | Lessard et al. .............. 211/74 |
| 5,620,561 A | | 4/1997 | Kuhn et al. ................ 159/47.1 |
| 5,648,271 A | * | 7/1997 | Kempe |
| 5,736,105 A | * | 4/1998 | Astle ........................ 422/100 |
| 5,897,838 A | * | 4/1999 | Kempe | 
| 5,935,859 A | * | 8/1999 | Elliott et al. ................ 436/54 |
| 5,989,499 A | * | 11/1999 | Catanzariti et al. .......... 422/63 |
| 6,039,211 A | * | 3/2000 | Slater et al. .................. 222/1 |
| 6,066,232 A | * | 5/2000 | Mohr et al. |
| 6,083,761 A | * | 7/2000 | Kedar et al. ................ 436/178 |
| 6,150,158 A | | 9/2000 | Bhide et al. ............. 435/286.3 |
| 6,132,582 A | * | 10/2000 | King et al. ................. 204/604 |
| 6,146,595 A | * | 11/2000 | Mikulsky |
| 6,238,627 B1 | * | 5/2001 | McGowan et al. |

* cited by examiner

Primary Examiner—Jill Warden
Assistant Examiner—Brian R. Gordon
(74) Attorney, Agent, or Firm—Cislo & Thomas LLP

(57) ABSTRACT

A laboratory evaporator device is disclosed which is modular in form so that the modular member supporting depending, upraised hollow needles or tubes through which evaporating fluid is conducted, may be individually sterilized and cleansed to thereby forestall cross-contamination. The laboratory device is simple in use, of relatively low cost and is of rugged construction.

34 Claims, 17 Drawing Sheets

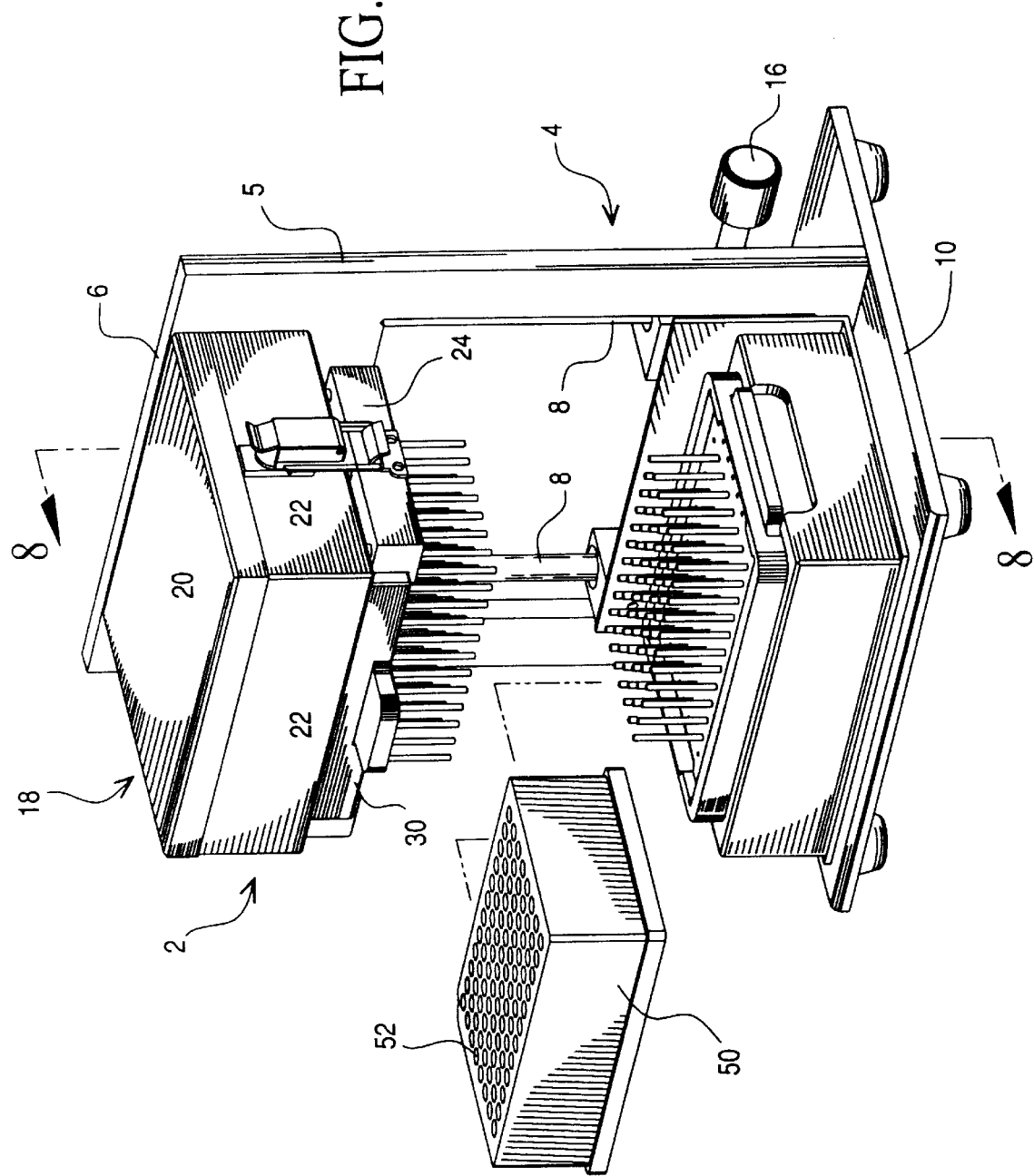

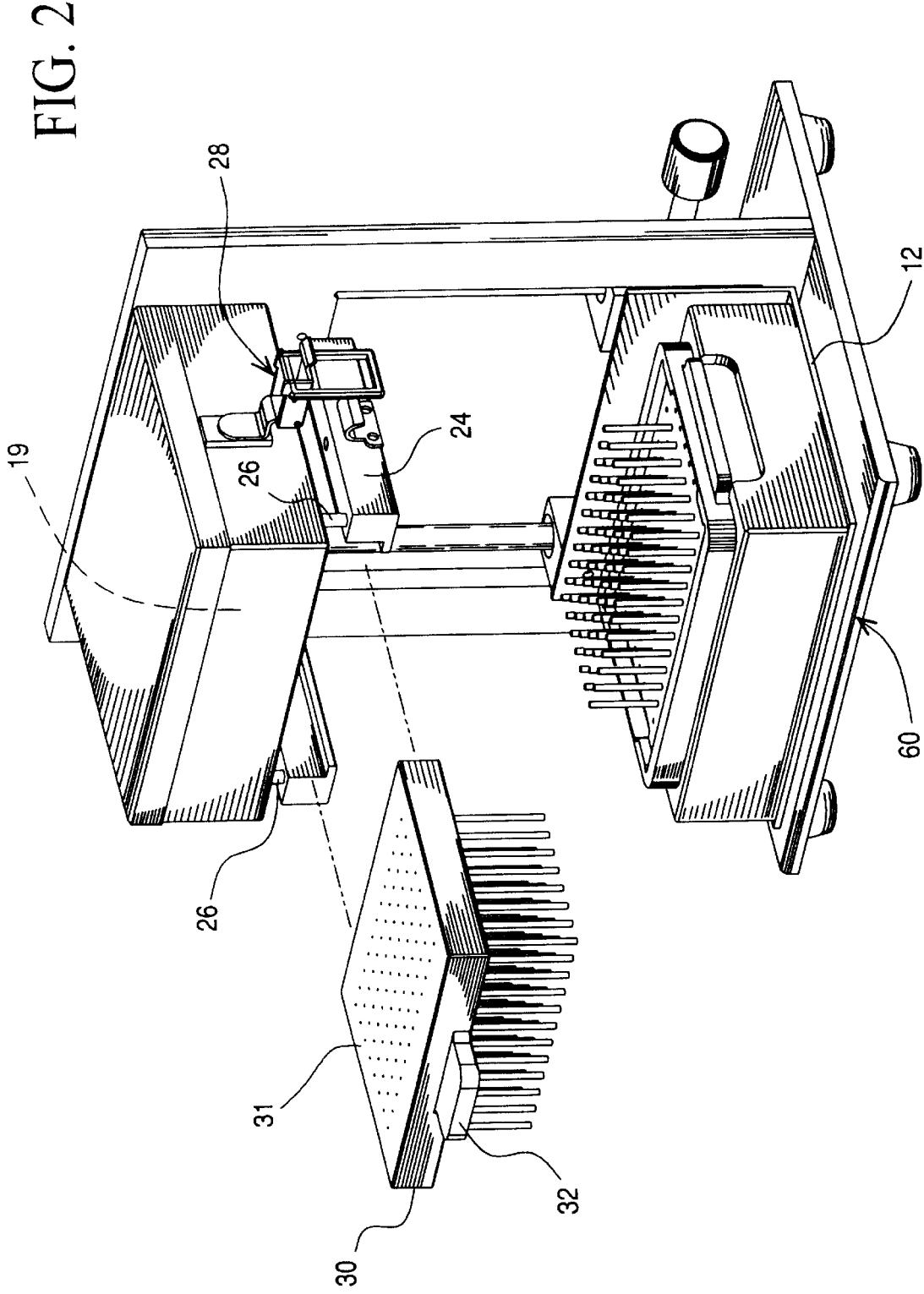

SOLID PHASE EVAPORATOR DEVICE

BACKGROUND OF THE INVENTION

1. Field of the Invention

This invention relates to laboratory devices and more particularly to a evaporator device of the type useful for an array of specimens or samples in the liquid form, having entrained solids, which are sought to be reduced so as to evaporate the diluent and leave behind the residue for further testing, wherein the device allows for evaporation in a positive, direct and controlled manner.

2. Description of the Related Art

With increasing research activity due in part to federal funds being provided to implement research in various areas, it becomes abundantly necessary to have samples for various test procedures. With the extreme activity in molecular biochemistry, it becomes necessary to test seriatim, a plurality of samples using various techniques, all in an expeditious and orderly manner.

Heretofore laboratory workers have had to take individual test specimens and evaporate samples in order to get the working residue from which other testing could be made. These methods have been slow and cumbersome and has usually entailed singular handling of individual samples and heating thereof by way of Bunsen burners or the like, or by introducing a fluid such as air or inert gas, heated or otherwise, in order to accelerate the evaporation process.

With the need to produce a plurality of samples for varying test procedures, multi-compartment assay or specimen containers have been developed for containing a plurality of measured specimens in each of the compartments. Thus there is a need to have a simple, relatively low-cost, easily maintained laboratory device that will accomplish controlled and direct evaporation of liquid samples contained in the plurality of wells of the multi-compartment assay trays.

U.S. Pat. No. 5,100,623 issued to Friswell is directed to a Laboratory Evaporation Apparatus. As shown in the Drawings, a support rack 15 is mounted in the basin 14 and retains a plurality of vessels 16 having openings at their upper ends for receiving liquid and solid compositions. Also defined by the front housing portion 12 is a vent 17 that communicates through an exhaust fan with an exhaust port in the rear housing portion 13. A tray-shaped transparent cover 18 is pivotally mounted on the rear housing portion 13 and can be pivoted from an open position shown in FIG. 1 into a closed position completely covering the basin 14 and the vent 17. Mounted in a rear portion of the cover 18 is a bracket assembly 19 that supports a combined gas and liquid supply line assembly 21. Included in the supply line 21 assembly are a plurality of elongated nozzles 22 rigidly supported by the bracket 19. Upon closure of the cover 18, each of the nozzles 22 is arranged to enter the open top of a different one of the vessels 16 in the manner shown in FIG. 2.

U.S. Pat. No. 5,514,336 issued to Fox is directed to an Automated Evaporator for Chemical Analyses. As shown in FIG. 1, the evaporator 20 is a turntable 22 that rotates a housing containing a heat transfer fluid, or a fluid bath 24, a carousel 26, and a gas distributing manifold 28. Adjacent to fluid bath 24 is a sensor arm 32 and a sensor control 33. Carousel 26 is situated in a fluid 44 such that sample containers 42 are not completely covered by fluid 44 within fluid bath 24. Manifold 28 is used for simultaneously distributing a drying, preferably non-oxidizing gas into each container of sample containers 42, shown in FIG. 3. Manifold 28 has a circular plate 56, shown in FIG. 1, connected to base 46 and generally parallel to carousel 26. Tubing lengths 57 and capillaries 58 direct drying gas from base 46 to sample containers 42 at a rate preferably great enough to drive off any oxygen from the air, but not so great as to cause splashing of the sample.

U.S. Pat. No. 5,260,028 issued to Astle is directed to a Method and Apparatus for Effecting Solid Phase Extraction. As shown in the Drawings, the instrument 10 is mounted on a table or support 11 therefore and comprises a first housing member 12 having a display panel 13 thereon, which may include a read-out device 14 and depressible buttons 15 which will actuate switches to call for a given sequence of operation. A compartment 16 is provided to house a plurality of reagent or eluate containers 17. Supported on housing member 12 is a rack or container 19 for tubes 20 containing aspiration tips. As shown in FIG. 1, an aspiration tip 23 is fitted to an aspiration nozzle. With reference to FIGS. 2, 3, 4, and 5, a cassette 34 is illustrated. The cassette 34 is a molded one-piece structure having distinct areas or tubes 35, 36, 37, 38, and 39, with interconnecting webs 40 and a generally rectangular base 41 to permit upright support 9. FIGS. 10 and 11 show a second magazine or tray 70 for in-feeding racks 51 containing eluent receiving tubes 51. Magazines 29, 30 are mounted on a slide 71 driven by the piston rod 71 of cylinder 71. FIG. 11 also shows, in part, a spent cassette out-feed magazine 73.

U.S. Pat. No. 5,620,561 issued to Kuhn et al. is directed to Vortex Evaporation. The vortex evaporator 10 comprises a chamber 14, a housing 16, a control panel 18, a lid 20, a heater 22, a gas supply system 24, and a drive mechanism 26 for providing a vortexing motion. The gas supply system 24 comprises gas feed tubes 30 which connect to a manifold 32, as shown in FIG. 5. The gas source preferably comprises an inert gas source for supplying purified gas across the solution contained within the containers 12 to prevent contamination of the solutions. With reference to FIG. 5, the vortex evaporator 10 also comprises a ventilation system 98 for venting the gas (e.g., nitrogen) and the evaporated solution fumes from the chamber 14. As shown in FIG. 9, the container holder 322 presents a plurality of cylindrical recesses 328 for snugly receiving the containers 12.

U.S. Pat. No. 3,977,935 issued to Kowarski is directed to a Method and Apparatus for Evaporating Liquids. As shown in FIGS. 1 and 3, the assembly includes an enclosure 11. The enclosure 11 comprises a lower body 12, an upper body 13 removable from the lower body 12, and a cover 36 secured to the top of upper body 13. A tube support 16 rests upon an upper flange portion of the lower body 12, as shown in FIG. 3. The tube support 16 includes a plurality of test tube receptacles 19 extending downward into the lower body 12, thereby forming a closed cooling chamber 20 within the lower body 12 defined by the side and bottom walls thereof, and the tube support 16.

The prior art. devices have not provided, as has the instant invention, for the ability to have a modular component supporting a plurality of pipette-type fluid tubes which may be easily cleansed for subsequent serial concentration processes.

SUMMARY OF THE INVENTION

The present invention remedies shortcomings and drawbacks found in the prior art by providing a relatively low-cost, structurally sound evaporator device which is easy to use. The evaporator device of the instant invention has a main manifold to which is coupled a modular member supporting a plurality of depending pipette-type tubes corresponding in number and alignment to the number of compartments or sample-containing sections of a multi-compartment assay tray. The assay tray is supported on a vertically-movable platen for positively and directly putting the depending hollow tubes or needles into close relationship or proximity to the interior volumes of the individual compartments of the assay tray.

Where the assay tray is so constructed so as to have adjacent spaces between side walls in the compartments, the device of the present invention has a lower manifold, again with upstanding hollow pipette-type tubes or needles, which similarly directs gas or fluid which may or may not be heated into the spaces, which are accessible through the bottom of the tray, between and adjacent the contiguous walls of the individualized compartments.

The modular construction of the component which may likely come into contact with the samples being worked upon is easily disassociateable from the manifolds and are easily sanitized or sterilized so that cross-contamination with subsequent specimens and samples is not likely to occur.

Additionally, the vertically moving platen which supports the assay tray may be brought in closer contact relationship with respect to the depending hollow tubes or needles so that the evaporating process may be carried out more effectively and efficiently.

The evaporating device of the present invention, though sophisticated in operation and ultimate function, is simple in mechanical terms leaving little or no room for mechanical breakdown. The evaporating device has the ability to be easily maintained and is relatively low-weight, and thus is mobile and may be used in various locations in the laboratory wherever a source of fluid, heated or ambient, such as air, nitrogen, etc. may be available. In other instances, the fluid need not be heated and the passage of a volume of fluid is relied upon solely for the evaporation action that takes place.

OBJECTS OF THE INVENTION

It is an object of the present invention to provide a solid phase evaporator device.

It is another object of the present invention to provide an easily-usable evaporator device to be used with a multi-compartment assay tray.

It is still another important object of the present invention to provide an easily used evaporator device for laboratory use wherein a plurality of depending hollow needles or pipette-type tubes are modularly mounted for ready disassociation with the assembly of the device for ease of sterilization.

It is still another more specific important object of the present invention to provide a desktop-type evaporator device for use in a laboratory, wherein heated fluids such as air or gas may be introduced into individual cells or compartments making up an assay test tray and wherein heated fluid may be injected about the side and bottom walls of the individual compartments making up the multi-compartment assay tray in order to speed and assist in the evaporative diluent reduction process.

These and other objects and advantages of the present invention will become apparent from the following specification and accompanying drawings.

BRIEF DESCRIPTION OF THE DRAWINGS

FIG. 1 is a perspective view of the solid phase evaporator device of the present invention with one type of assay tray being shown.

FIG. 2 is a view similar to FIG. 1, but showing the modular component which structurally supports the hollow tubes or needles which are aligned in rows corresponding to the rows of compartments of the assay tray.

DESCRIPTION OF THE PREFERRED EMBODIMENT(S)

Figure 3A:
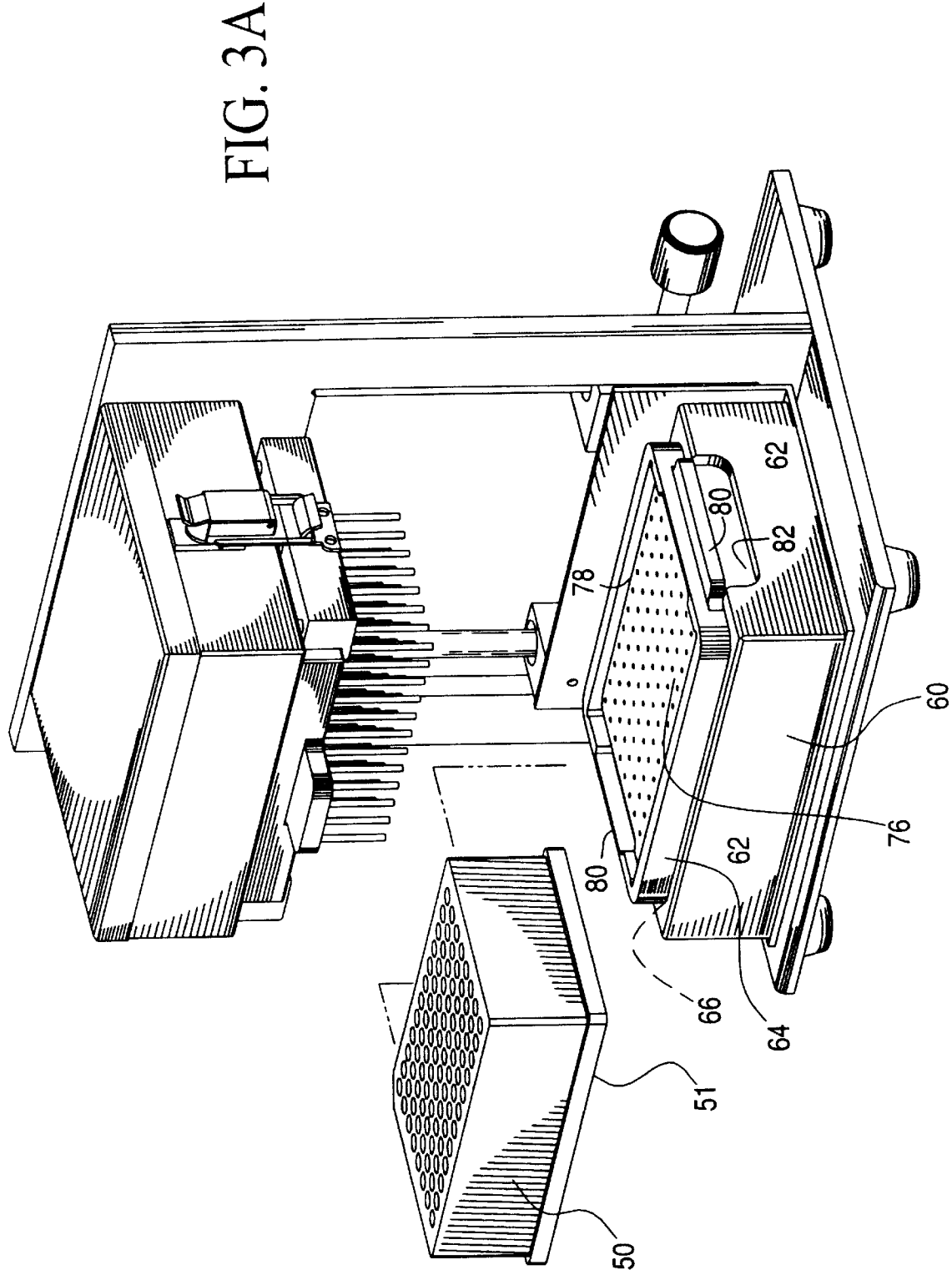
FIG. 3A is a view of the evaporator device shown in FIG. 1, but having the lower modular component, which supports the upraised hollow tubes or needles, turned over to receive a different type of assay tray.

The detailed description set forth below in connection with the appended drawings is intended as a description of presently preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Generally the invention relates to an evaporator device comprising the combination of a support member operatively supporting an upper fluid manifold having a plurality of fluid outlets. A base member is operatively secured to the support member by at least one vertical support, with the at least one vertical support operatively supporting a platen for incremental movable relationship with respect to the upper fluid manifold. The platen is adapted to support a multi-compartment assay tray for aligned and selected movable relationship relative to the plurality of fluid outlets.

Using the device of the present invention, a process of recovering solids from liquids by evaporating liquid is intrinsic in the device and entails placing liquid samples in individual compartments and directing gas, heated or ambient, into each of the individual compartments through individual ports aligned with each of the individual compartments, and then selectively varying the distance between the liquid surface in each of the individual compartments and the individual ports through which gas is directed and then recovering a solid or less liquid residue sample from each of the individual compartments for further testing.

Referring to the drawings, it will be seen that the evaporator device 2 of the present invention comprises a support member generally indicated as 4 having an upper support span 6 with vertical support members 5 with space-opposed rods 8 all supported from base member 10.

The support member 4 may be made up of individual components or may be a singular member. For example, the upper support span 6 and vertical support 5 may be as one-piece, as shown, or fabricated of individual components. Likewise, the base member 10 may also be a separate component as shown, or may be fashioned in one piece. Where individual components are utilized, the same may be fastened by means known in the art, whether it be welding, screws, bolts, etc.

It will be noted that an L-shaped, in cross-section, platen 12 is positively supported by reason of being mounted to side guides 14 which are in captive relationship with spaced vertical support rods 8 such that the platen or table 12 may vertically move relative to the upper support span 6, as will be described.

A thumbscrew and friction bolt 16 provides a means whereby turning of the thumbscrew 16 will cause frictional engagement with the support rod 8 so as to retain in frictional engagement, the table or platen 12 in preselected, predetermined relationship with respect to the upper portion of the device 2.

Supported from the upper span 6 is upper fluid manifold 18 having a top wall 20 and side walls 22 to thereby ultimately form an interior compartment 19 as will be seen.

Figure 14:
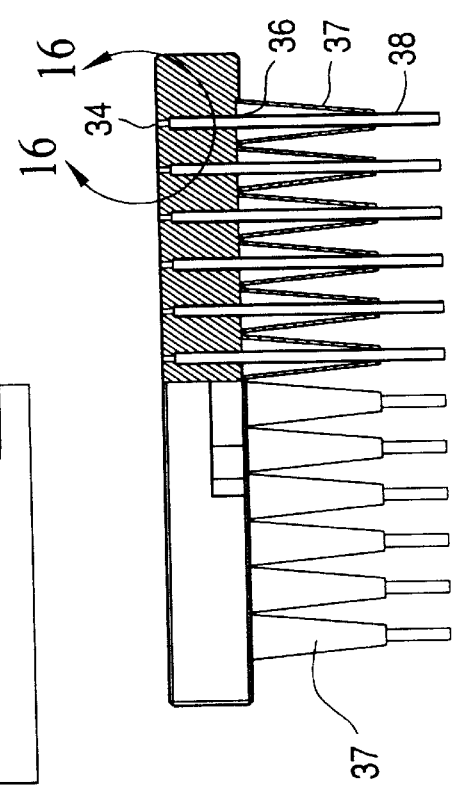
FIG. 14 is a view taken along line 14—14 of FIG. 13.
Figure 15:
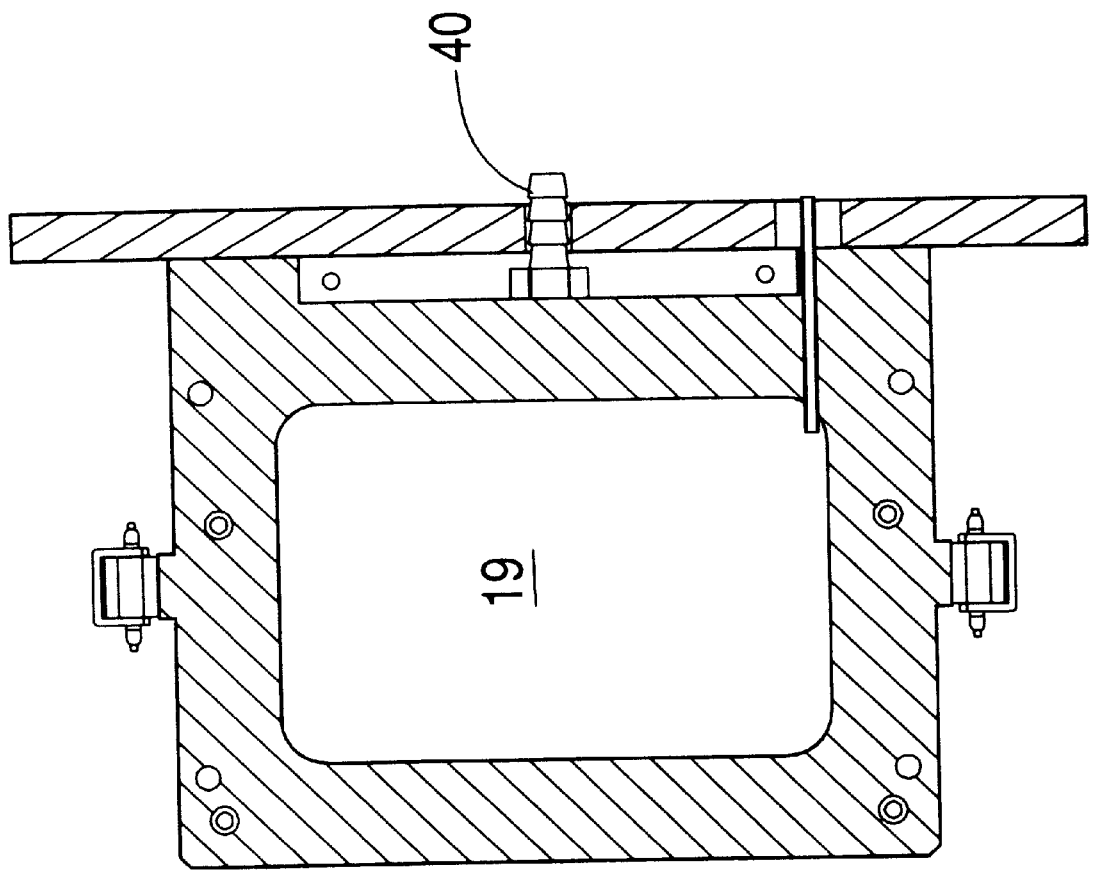
FIG. 15 is an enlarged cross-sectional view of the upper manifold and taken along line 15—15 of FIG. 5.
Figure 16:
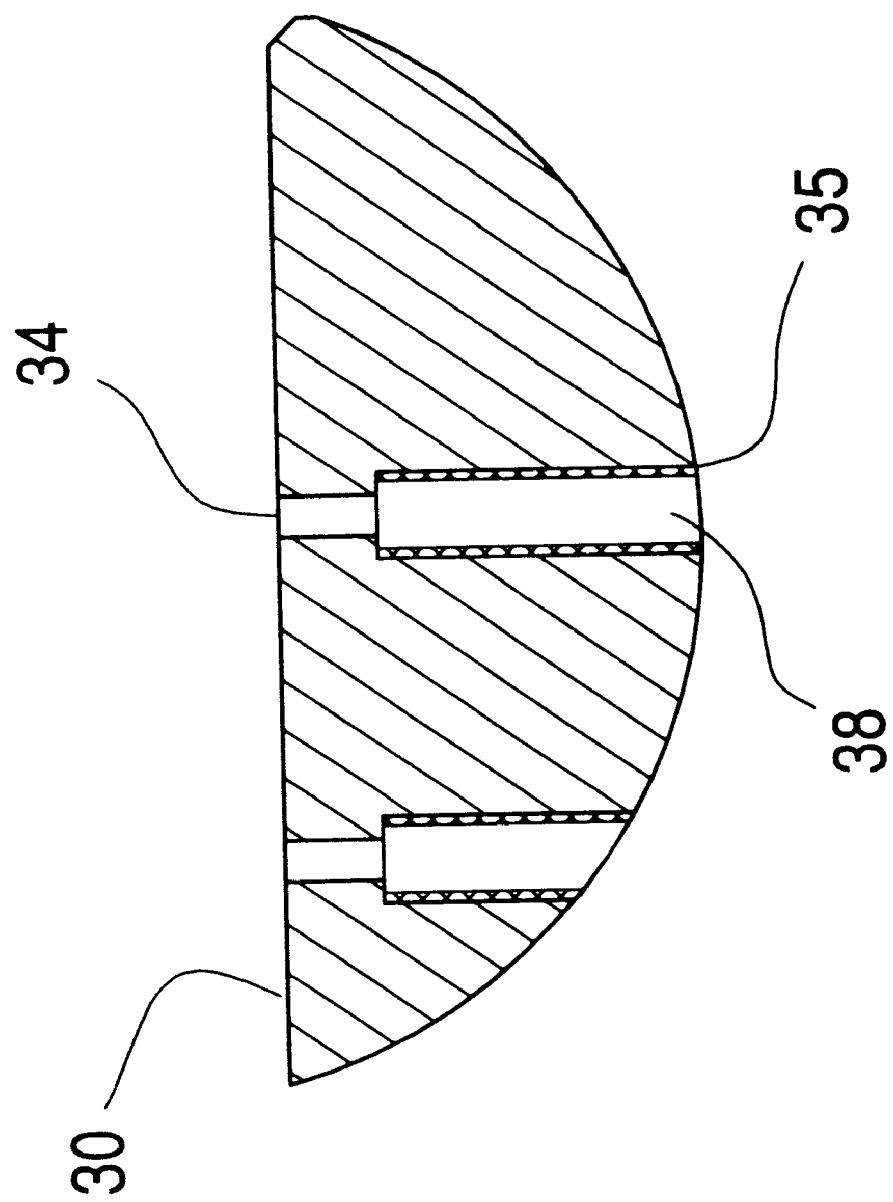
FIG. 16 is an enlarged view taken along line 16—16 of FIG. 14.

The interior compartment 19 of the upper manifold 18 is formed by reason of hollow needle or pipette support member 30 having a plate-like configuration and which has a plurality of apertures or through bores 34 extending therethrough. In one instance, enlarged lowermost apertures 36 support one type of hollow needle or pipette as best seen in FIG. 14. The number of apertures 34 will correspond in number to the number of hollow tubes or needles that need to be supported within the bores 36 as will be seen.

The hollow needle support member 30 has opposed side brackets 24 which brackets 24 are supported from the side walls 22 of upper fluid manifold 18 in limited vertical movement fashion by reason of opposed rods 26. Thus when the opposed support brackets 24, which retain hollow needle support member 30, are moved upward, the interior compartment 19 is formed, into which heated fluid or like is introduced, as will be seen.

To this end, it should be noted that the side walls 22 of upper fluid manifold 18 have a simple snap and hinge connector on opposite sides thereof so as to enable opposing lateral bracket members 24 to be moved upwardly from the position shown in FIG. 2, once the hollow needle support member 30 is releasably and slidably placed therein to be moved vertically upwardly into the position shown in FIG. 1 so as to form a fluid-tight connection between the upper surface 31 of the hollow needle support member 30 to thereby form relatively fluid-tight gas chamber 19. Sealing, O-ring 41 or the like, (FIG. 8), may also be utilized to insure against fluid leakage from compartment 19.

The hollow needle support member 30 has a generally plate-like rectangular configuration with an extending tab 32 for ease of manipulation by the thumb and fore finger of the operator of the device 2.

It will be noted that the hollow needle tube or pipette support member 30 in this instance may be composed of medical grade, heat and chemical resistive plastic wherein a plurality of apertures 34 are placed in aligned rows 33 and 35 and wherein, as earlier indicated and referring to FIG. 14, the through bores 34 are smaller in diameter than the lower portion thereof which is enlarged to support hollow needles, pipettes or tubes 38. The number of hollow needles or depending pipettes 38 through which, as will be seen, a fluid is directed from the upper manifold 18 corresponds in number to the cells or compartments found in assay tray 50.

In the embodiment shown in FIG. 1 assay tray 50 has a plurality of circular configured cells or compartments 52 and each cell or compartment 52 is cylindrically shaped and has a space 54 between each of the cylindrical walls of the compartments 52 for purposes which will be described.

Figure 3B:
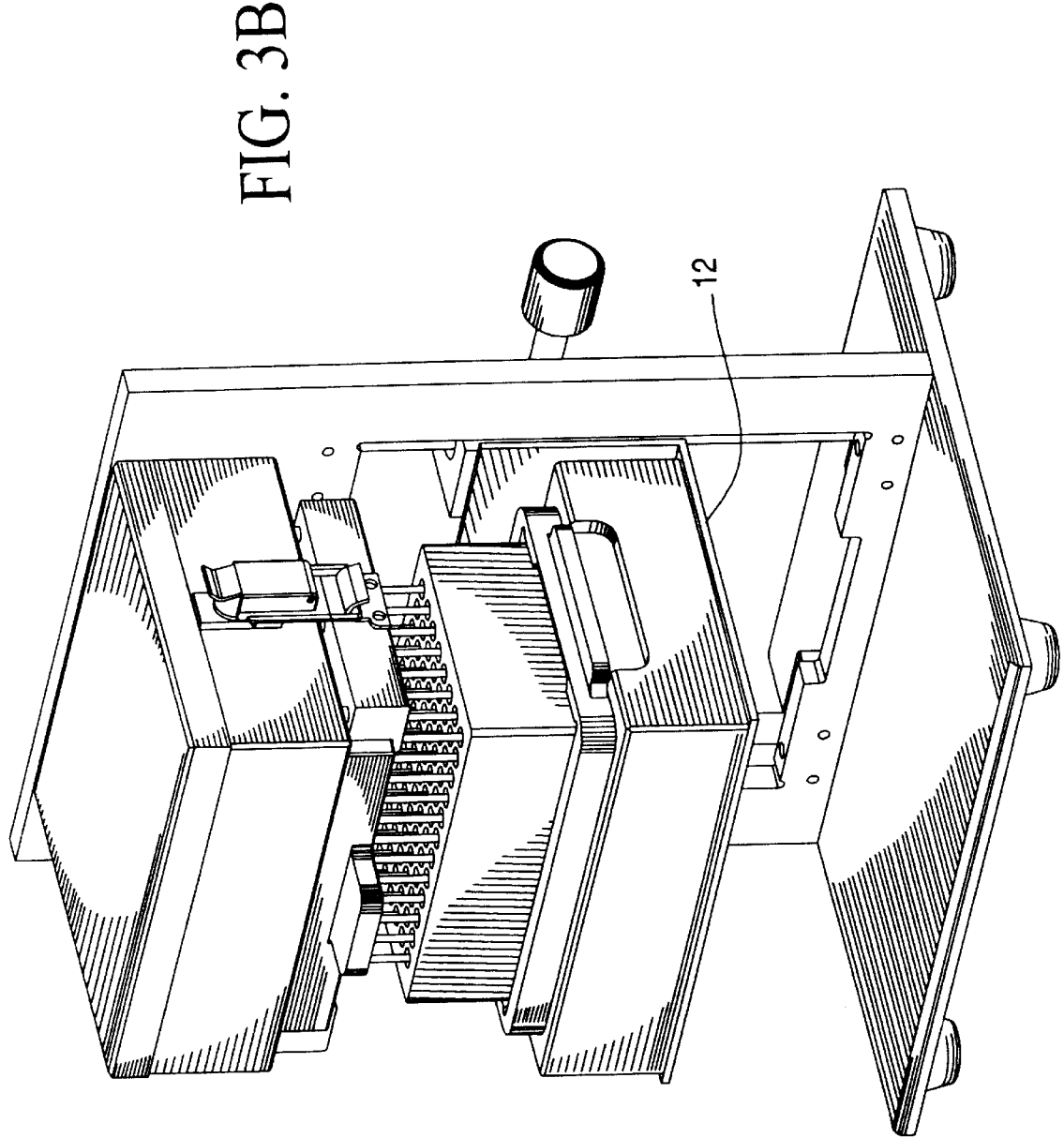
FIG. 3B shows the device of the invention with the platen in the upraised position, so as to have the depending hollow tubes or needles partially inserted into the individual wells or compartments making up the assay tray.
Figure 4:
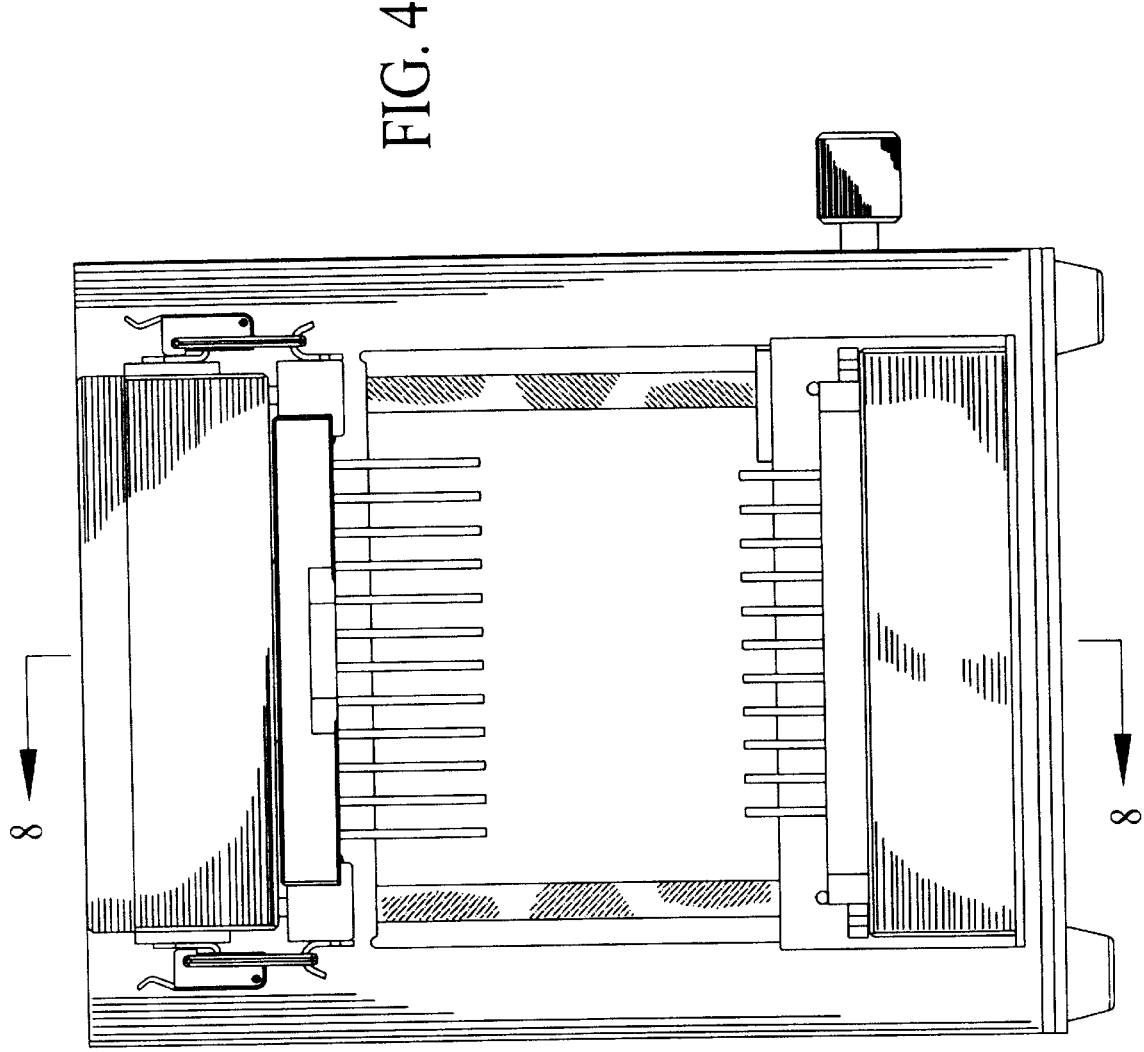
FIG. 4 is a front view of the device shown in FIG. 1 with the assay tray removed for purposes of clarity.
Figure 5:
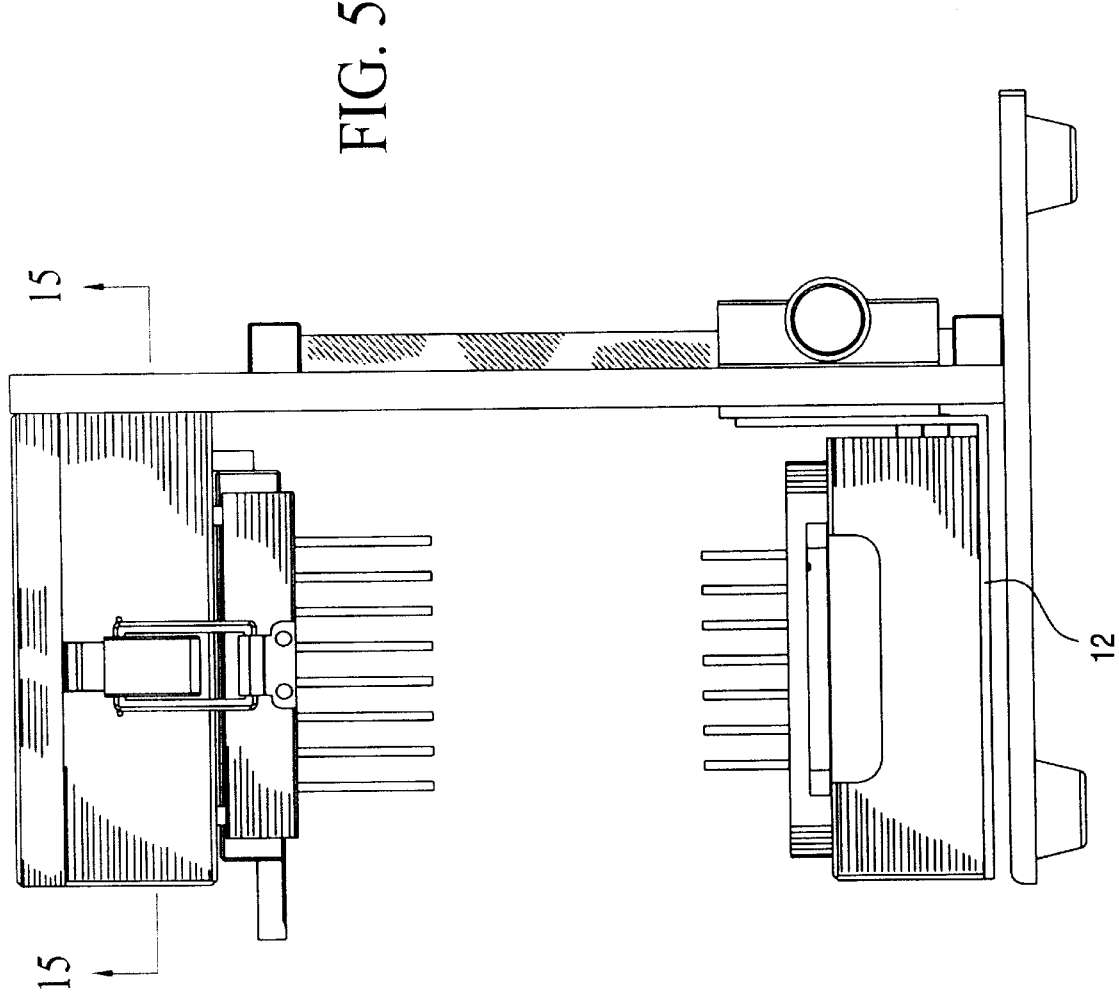
FIG. 5 is a side elevational view of the device shown in FIG. 1.

It should be noted that the upper fluid manifold 18 has a fluid inlet 40 by which a fluid, heated or otherwise such as air or nitrogen or other inert gas may be introduced into the interior 19 so that the heated fluid may be dispersed or directed outwardly from the interior compartment 19 of upper manifold 18 and thence downwardly through the orifices or apertures 34 and then through the depending hollow tubes 38 and thence into the individual cells or compartments 52 as best seen in FIG. 3B.

The device 2 as just described will function to permit evaporation of diluent from liquid or semi-liquid samples disposed in one or more of the individual compartments 52 of assay tray 50. However because assay tray 50 is of the type that has spaces 54 between the individual cells 52, the versatility of the evaporator device 2 of the invention will now become apparent.

Figure 8:
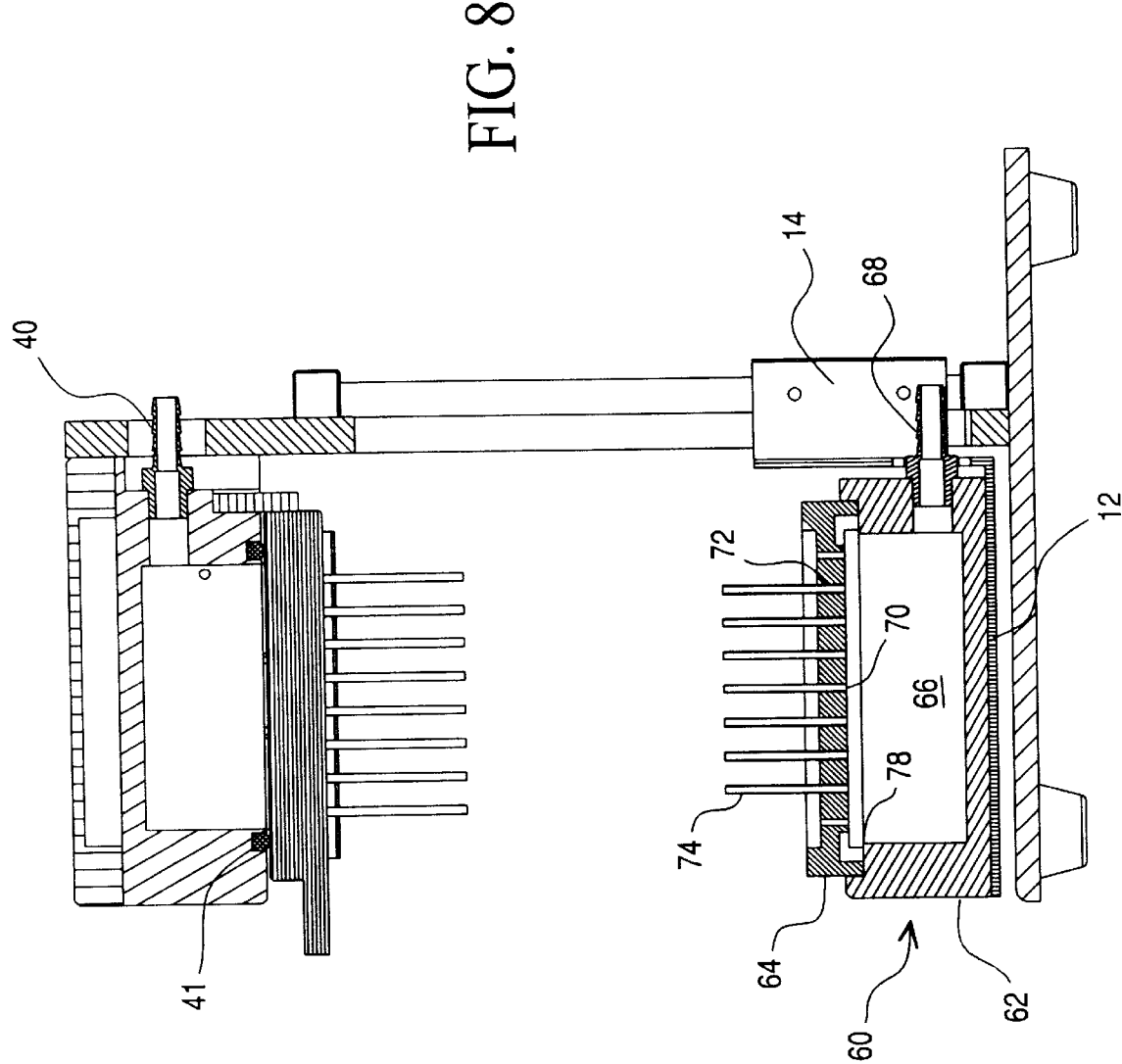
FIG. 8 is a cross-sectional view of the evaporator device shown in FIG. 1, taken along the line 8—8 thereof and showing more details of construction.
Figure 10:
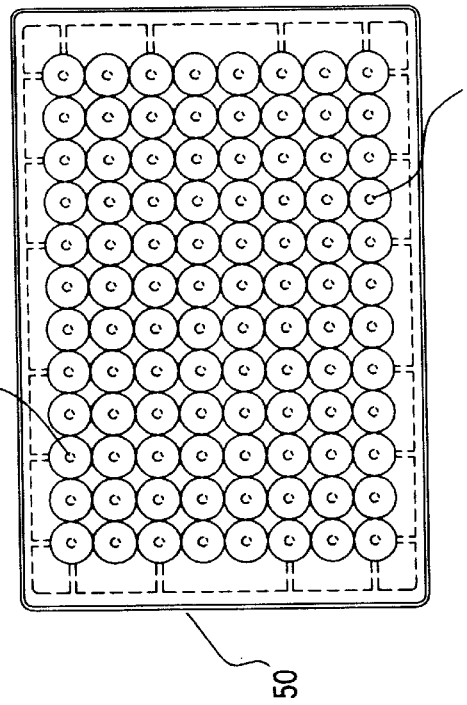
FIG. 10 is a top view of the assay tray shown in FIG. 9.
Figure 9:
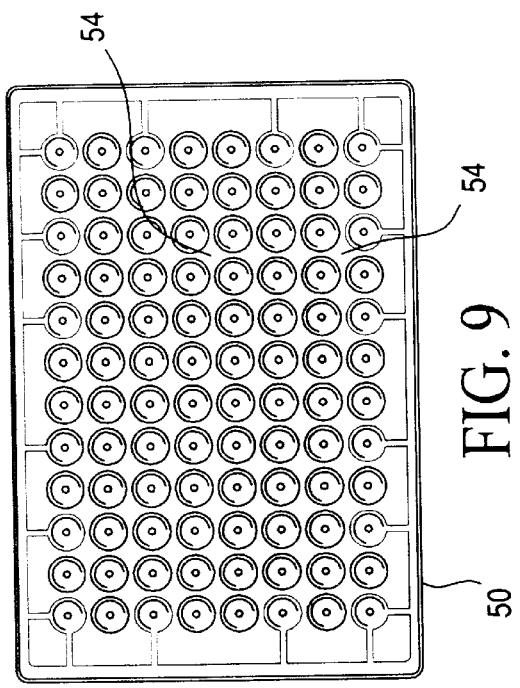
FIG. 9 is a bottom view of one type of assay tray as shown in FIG. 1.
Figure 11:
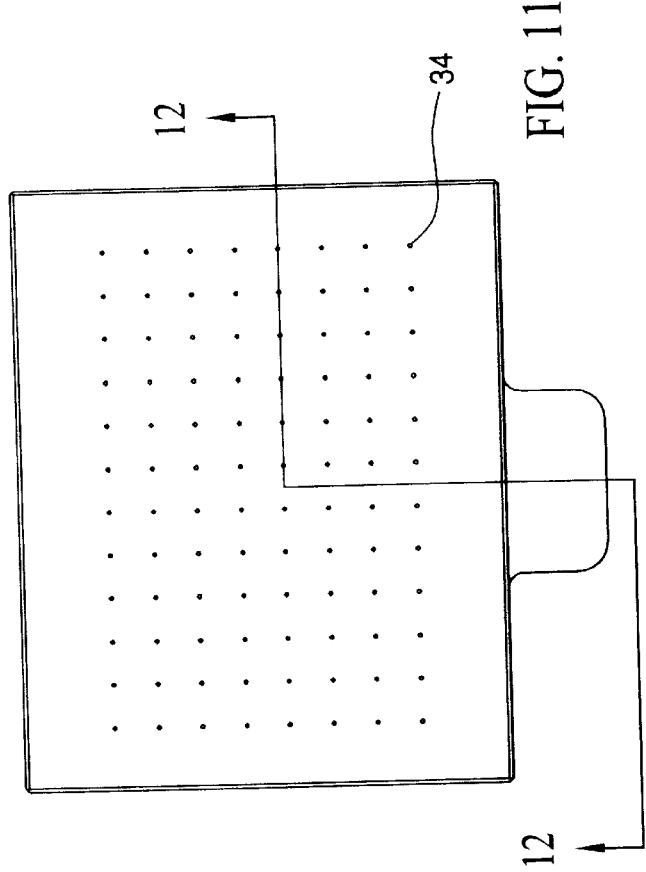
FIG. 11 is a top view of the upper manifold modular unit supporting the depending hollow tubes or needles.

Referring to FIG. 8, it will be noted that associated with platen or table 12 is lower manifold 60 in this instance being fabricated of the same type of material as upper manifold 18 and having side walls 62 and in this instance being integrally molded of the laboratory grade plastic heretofore described and wherein a removable top 64 is adapted to be seated on the perimetric shoulder 78 formed in the upper portion of side walls 62 of member 60. The member 64 forms, in conjunction with side walls 62, an interior compartment 66 which is connected via connector 68 to a source of heated fluid not shown.

Unlike the upper fluid manifold 18, the upper wall member 64 may have a plurality of constant diameter through bores 70 with portions 72 each supporting hollow tube or needles 74 very much like the alignment and positions described for hollow tube support member 30, previously described.

The member 64 is removable much like the lid of a box and may be turned over so as to provide a flat receiving surface 76 best seen in FIG. 3A and having upstanding inwardly spaced upper perimetric wall 78 to better receive and seat the bottom, for example, of assay tray 50 particularly where the assay tray does not have the intermittent walls or spaces 54 to allow for the placement or reception of the upstanding hollow tubes or needles 74 through which heated fluid such as air, nitrogen or other inert gas may be flowed.

Referring to FIG. 8, it will be noted that the upper member 64 supporting the hollow tubes 74 has lateral tabs 80 for ease of handling and to provide ease of access to these tabs 80, the two short side walls 62 of lower manifold 60 have grooves or indentations 82. (FIG. 3A)

Figure 12:
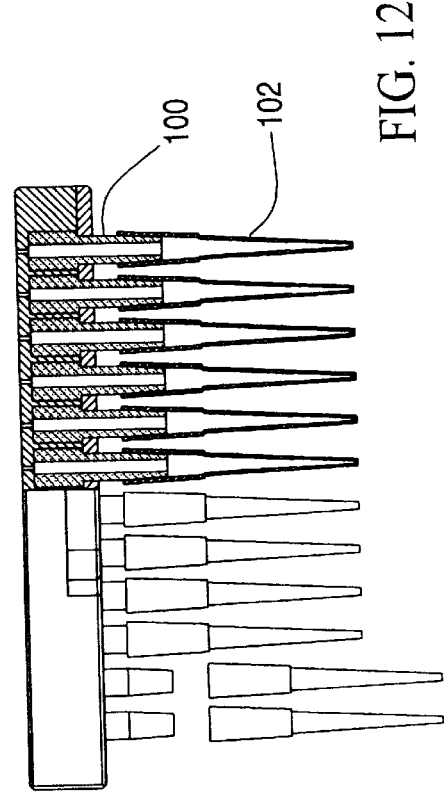
FIG. 12 is a view taken along line 12—12 of FIG. 11.
Figure 13:
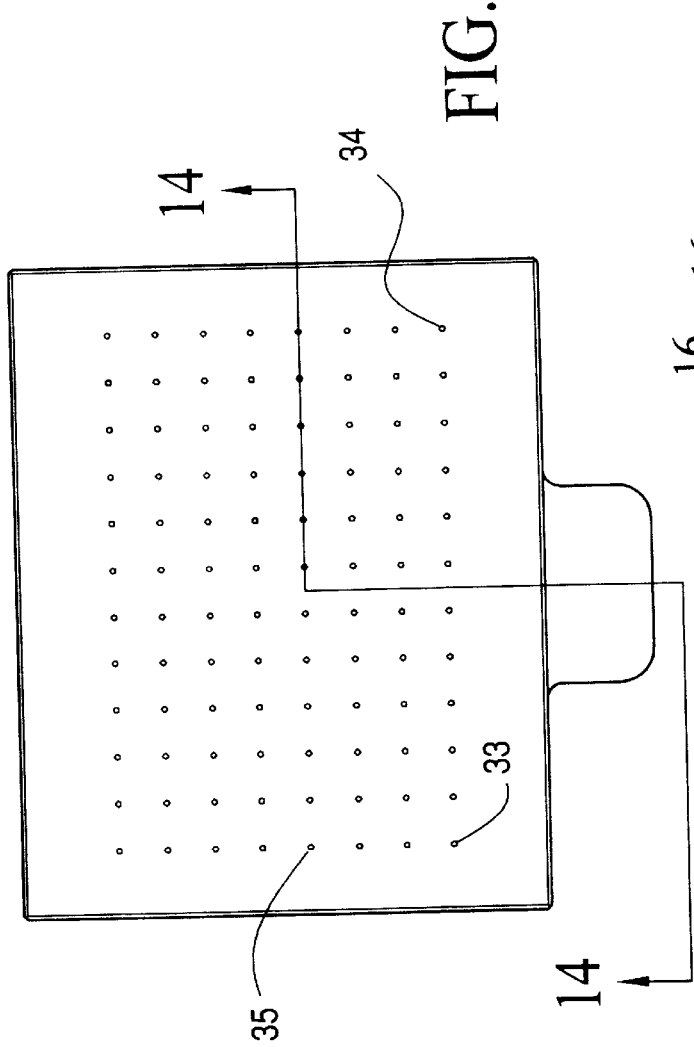
FIG. 13 is a view similar to FIG. 11, but showing a different type of hollow needle, pipette or tube.

Again referring to FIG. 8 the number of hollow tubes 74 are equal in number to the spaces 54 formed between each of the cells 52 of assay tray 50:

Referring to FIG. 12 another embodiment of a specific type of hollow tube 100 is shown which in this case is of shorter length and is configured so as to have plastic disposable tips 102 frictionally and releasably secured thereto so that instead of subjecting the upper hollow needle or tube support member 30 to sonic cleaning or other sterilization, the extenders 102 because they are plastic and disposable may be taken off and discarded with new tips 102 put in place so as to prevent any possibility of cross contamination with respect to subsequent evaporation of different test samples and specimens using the device 2.

The apertures or orifices 34 shown in the upper hollow needle support member 30 is as indicated a through bore 34 which is smaller in diameter at the upper end than the lower portion 35 within which is disposed the hollow needle pipette or tube 38.

Referring to FIG. 14 an insulator 37 is provided, for hollow needle 38, In this instance insulator 37 is comprised of an open ended, conical molded plastic member disposed around each of the hollow needles, tubes or pipettes 38 and acts as insulative members to prevent heat loss of the heated gas which is introduced into the interior compartment 19 of the upper manifold 18 for disposition through the ends of the hollow needles or tubes 38. Obviously the conically shaped plastic insulators 37 provide air insulative attributes by reason of the air space surrounding the conical insulator 37 relative to each of the depending needles or tubes 38.

Figure 6:
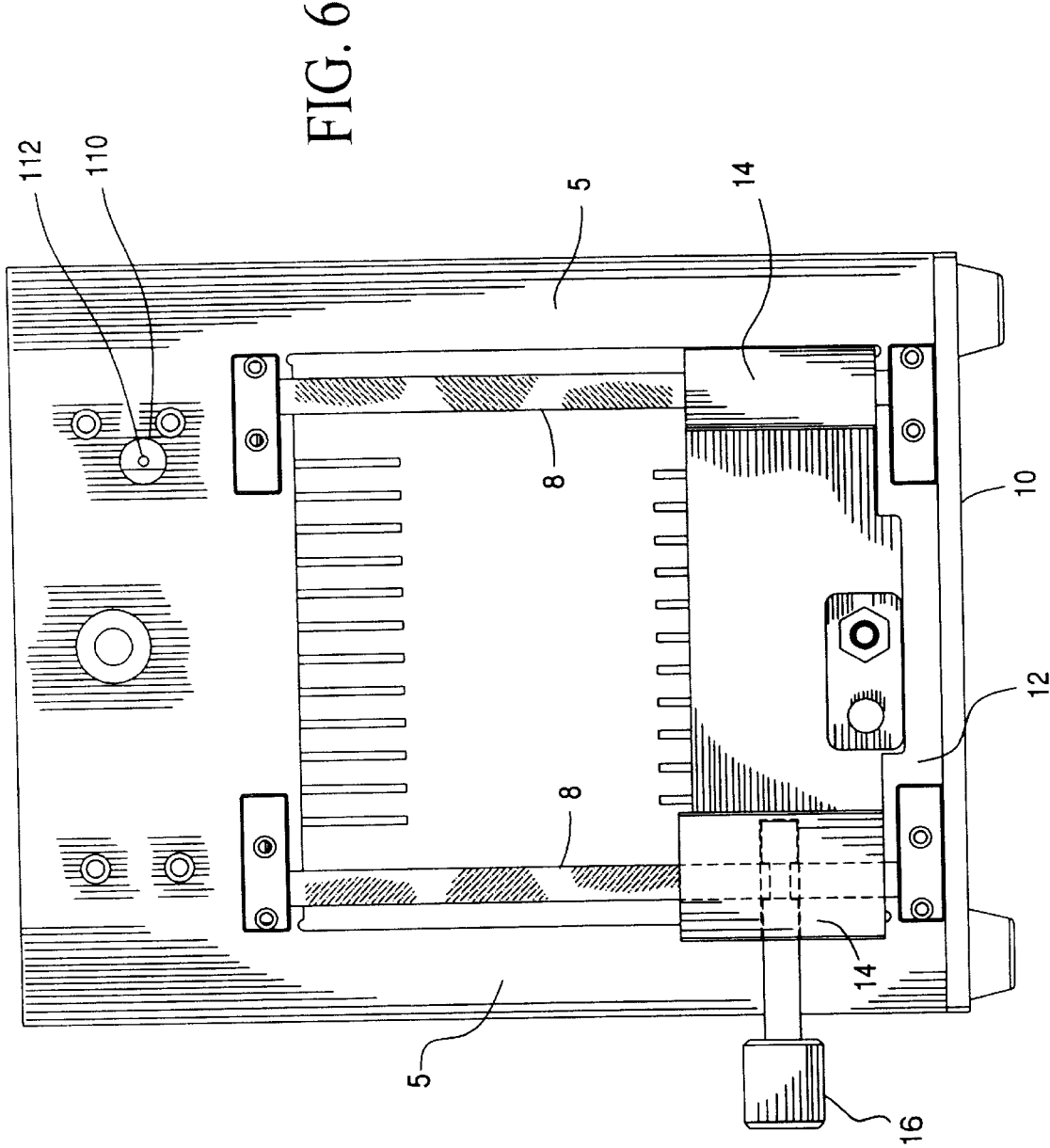
FIG. 6 is a back view of the evaporator device shown in FIG. 1.
Figure 7:
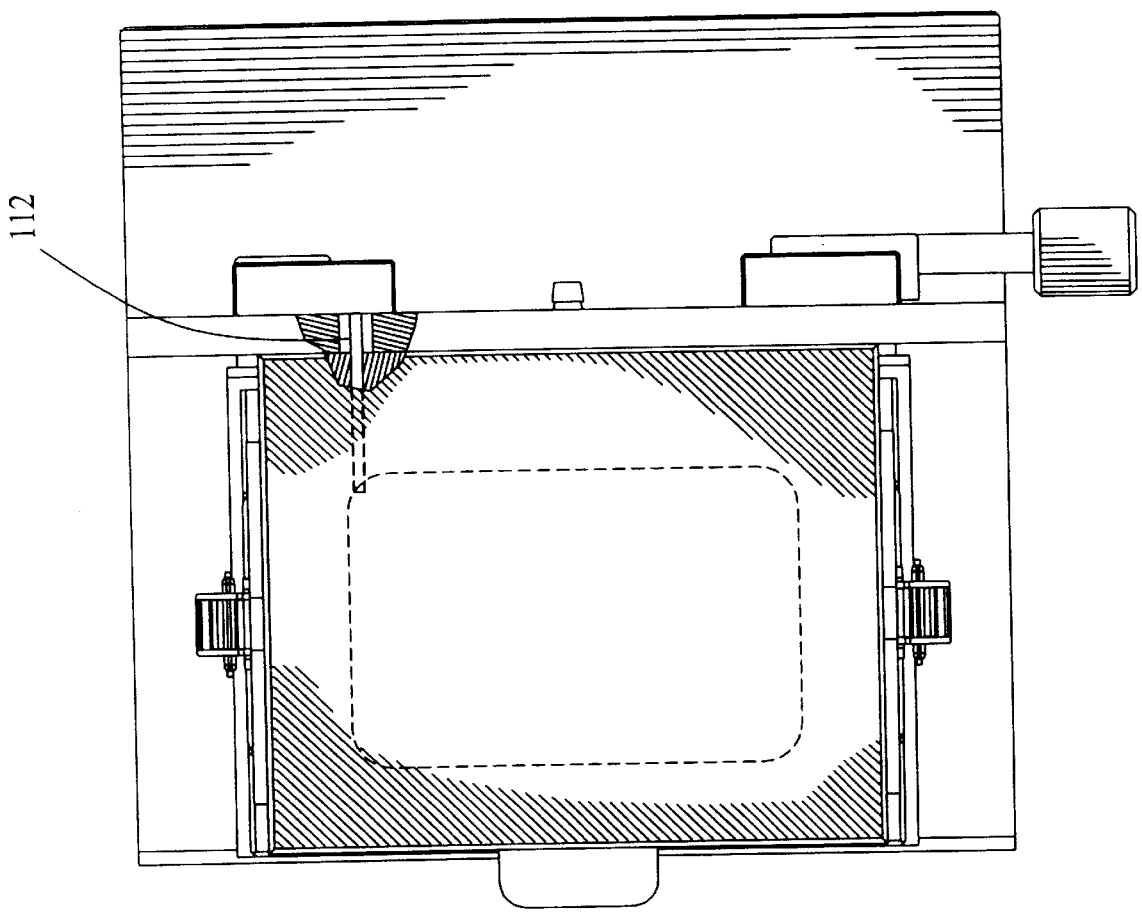
FIG. 7 is a top view in partial cross-section of the evaporator device shown in FIG. 1.
Figure 18:
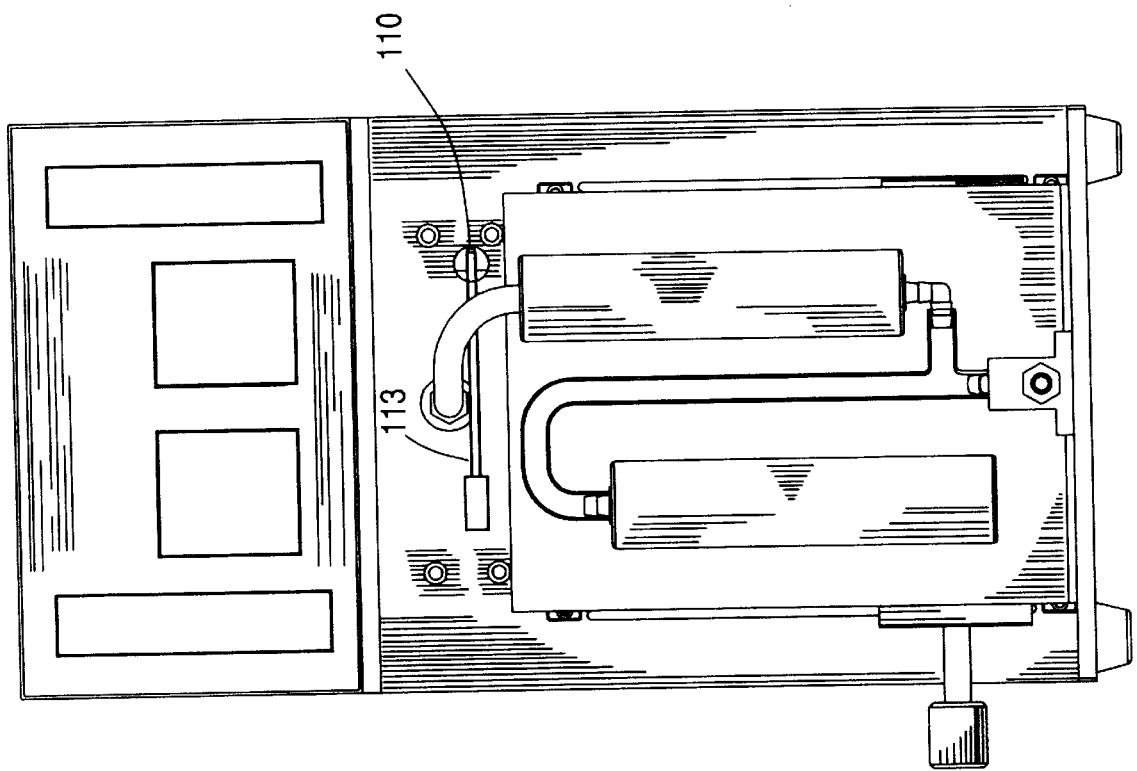
FIG. 18 is a back view of the evaporator device shown in FIG. 17.

Obviously the device 2 of the invention may utilize and employ various instrumentation in order to insure proper efficient use of the device. One such auxiliary embellishment may comprise, as best seen in FIGS. 6 and 18, an inlet 110 for a probe 112 which may be attached to a thermal couple 113 or the like, in order to determine the temperature of the heated fluid being introduced into the upper manifold 18. The probe 112 may be further calibrated with means known in the art to insure or ascertain the temperature of a heated fluid emanating from the termini of each of the depending hollow needles or tubes 38.

Figure 17:
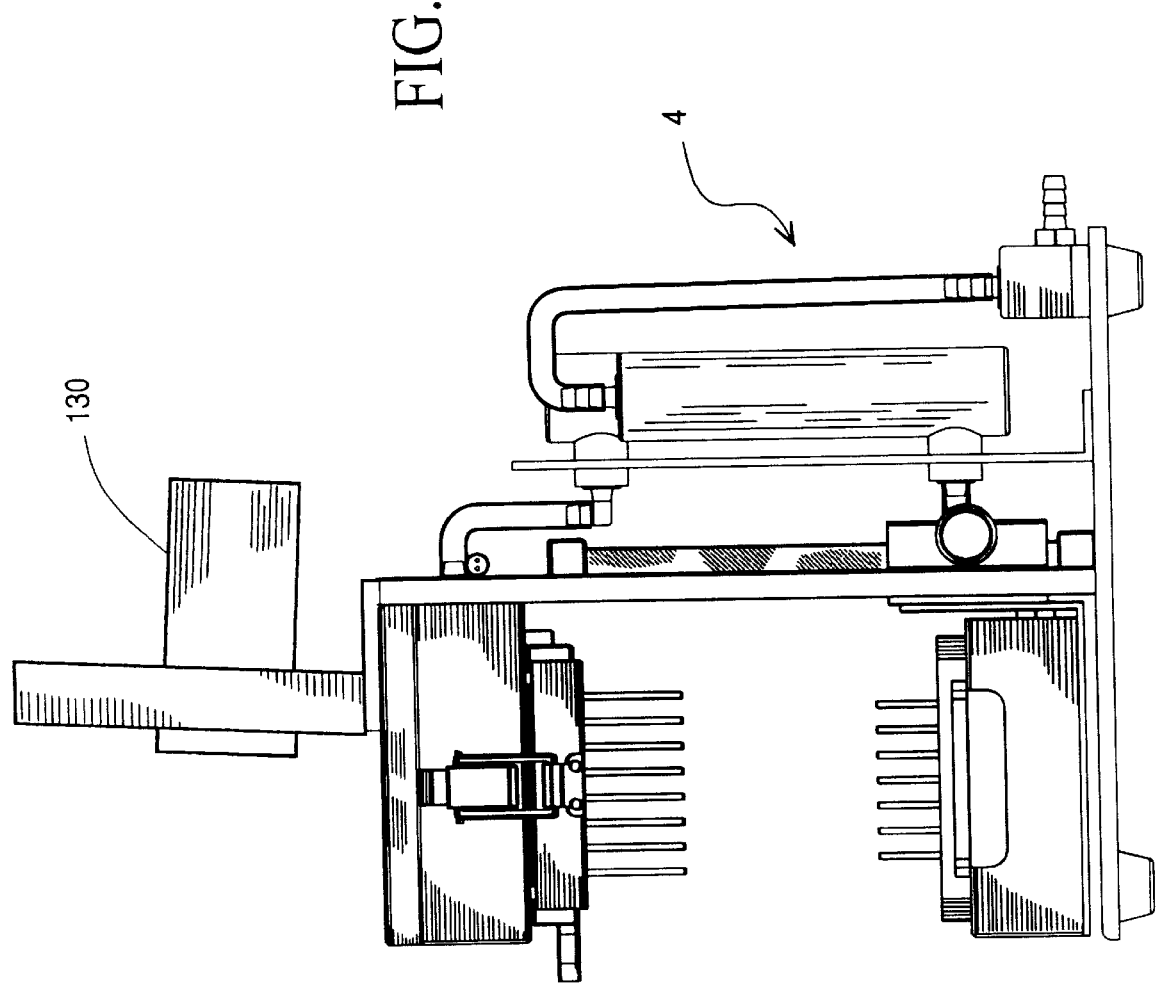
FIG. 17 is a side view of the evaporator device of the present invention showing auxiliary controls as may be necessary to effectively operate the device.
Figure 19:
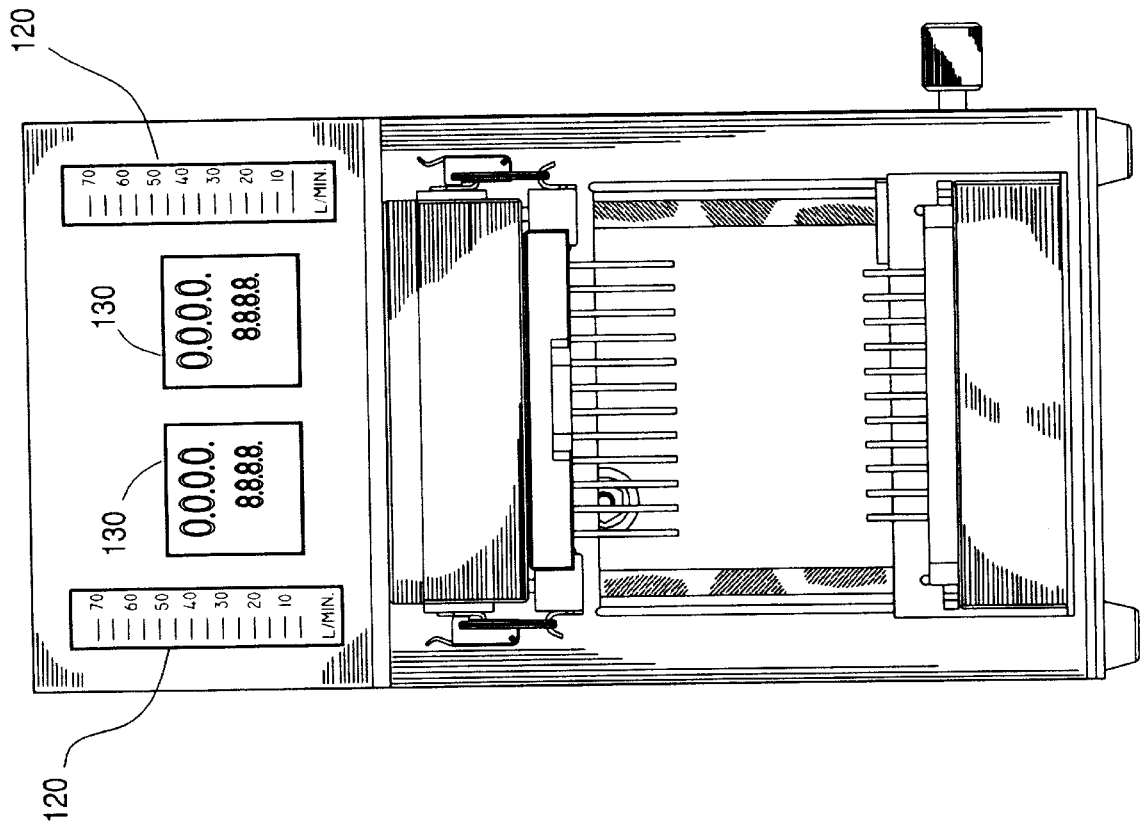
FIG. 19 is a front view of the evaporator device shown in FIG. 17.

Referring to FIGS. 17, 18 and 19 it will be noted that the device 2 has positioned on the base or stand 4 instrumentation such as gas flow meter 120 and temperature regulator 130 which of course are in turn connected to a fluid supply of heated gas such as nitrogen, air or the like. The instrumentation contained within the controllers 120 and 130 have suitable operative connections to other devices not shown and to supplies of electrical power.

In the utilization of the device 2, for example as shown in FIG. 1, the device is readied by taking the hollow needle support member 30 and placing it in association with the side brackets 24 as shown in FIG. 2 and then raising the same into a fluid tight relationship to form the interior compartment 19 by reason of the hinge and snap members 28. If the assay tray is of the type having spaces between each of the cells from the bottom, the configuration of the device 2 is as shown in FIG. 1, the assay tray 50 is placed on the lower manifold 60 so as to orientate each of the upstanding hollow needles or tubes 74 between the individual cells 52 of assay tray 50 and more specifically the plurality spaces of 54. The platen or table 12 with attached lower manifold 60 is then raised by hand to a level that is selectively and desirably determined by the technician, more specifically as shown in FIG. 3B. The depth of penetration of the depending hollow needles or tubes 100 into the individual open cells 52 of assay tray 50 will be visually determined by the amount of sample contained therein.

Upon placement of the platen 12 at the desired level the turnscrew or knob 16 is rotated so as to securely retain the platen 12 with the lower manifold 60 in place, again as seen in FIG. 3B.

Thereafter a fluid either at ambient or higher than ambient temperature is introduced into upper connector 40 which then allows passage thereof into the interior compartment 19 of upper manifold 18. The introduced fluid builds up a slight back pressure because of the size of the apertures or orifices 34 and the gas is then projected downwardly through the hollow tubes and needles 38 and thence into the interior of individual compartment or cells 52 to initiate the evaporating process. Periodically as the diluent is evaporated out of the individual cells 52 the platen with associated lower manifold, which is supporting the assay tray 50, may be manipulated by hand so as to vertically reposition the depending hollow needles or tubes so as to more effectively put the gas into contact with the surfaces of the samples which are to be evaporated.

Where the assay tray 50 is of the type described having the spaces 54 therebetween, at the same time that the process is initiated with respect to the upper manifold 18, fluid is introduced through the lower fluid connector 68 of the lower manifold 60. Preferably in this case the introduced fluid is heated gas such as air or nitrogen. Obviously heated gas or fluid such as air or nitrogen may also be introduced into the upper manifold 18 as previously described.

When a sample has dissolved solids in solvents such as an organic solvent such as methanol or acetyl nitrate, the heated gas that is introduced into either both upper and lower manifolds would be in the area of 37–60° C., depending on the sensitive nature of the samples. The pressure of the introduced fluid will vary of course depending upon the velocity desired and the size of orifices or passageways 34 but in most instances it has been found that a pressure of about 15–50 PSI is adequate.

Obviously temperatures and rates of flow will vary depending upon the size or capacity of the individual cells or compartments making up a multi-compartmented assay tray. In the instance where an assay tray is utilized that has spaces between the individual cells so as to accommodate the hollow tubes or needles of the lower manifold these have a 1 ml capacity whereas the other type of assay tray having rectangular configuration and not having spaces between the individual compartments will have a capacity of about 2 ml.

The aforedescribed methodology for carrying out the process with the described device is for illustrative purposes only, but it should be clear that a processing device has been disclosed for recovering solids from liquids by evaporating the liquid content thereof wherein a liquid sample is placed in individual compartments and heated fluid such as nitrogen or air is directed into each of the individual compartments through individual ports which are aligned with each of the individual compartments and then selectively varying the distance between the liquid surface in each of the individual compartments and the individual ports through which the heated fluid is directed whereby evaporation takes place and a recovery of solid residue in various forms and various concentrations may be recovered from each of the individual compartments.

When desiring to evaporate other samples and to negate the possibility of cross contamination the upper and lower manifold assemblies may be individually removed because they are in modular form and thereafter subjected to cleaning techniques either sterilization as is well known or through sonic cleaning. In the instance where disposable tips are used on the hollow tubes or needles these obviously are discarded and new ones utilized.

A device as heretofore described has been fabricated and used successfully in laboratories and such a device had the following parameters:

| DESCRIPTION | Overall Height | Overall Width | Overall Depth | Diameter Inside | Diameter Outside | Length | Material | Other |
|---|---|---|---|---|---|---|---|---|
| Upper Manifold Fluid Chamber | 2 | 5.842 | 4.782 | | | | Acetyl Co-Polymer | Alternate mat'l: Teflon |
| Needle Support Member | 0.625 | 4.922 | 4.737 | | | | Acetyl Co-Polymer | Alternate mat'l: Teflon |
| Needle Size-Upper Manifold | | | | 0.077 | 0.095 | 2.08 | 304 Stainless Steel | |
| Lower Manifold Fluid Chamber | 1.5 | 6.18 | 4.47 | | | | Acetyl Co-Polymer | Alternate mat'l: Teflon |
| Removable Top | 0.6 | 6.185 | 3.99 | | | | Acetyl Co-Polymer | Alternate mat'l: Teflon |
| Needle Size-Lower Manifold | | | | 0.077 | 0.095 | 1.7 | 304 Stainless Steel | |
| Base Plate | 0.25 | 8.25 | 12 | | | | | |
| Platen Vertical Travel-Maximum | | | | | | | | 3.950 Inches |
| Device Overall Size | 9.869 | 12.5 | 12 | | | | | |
| Maximum Operating Temperature | | | | | | | | 60° Upper, 80° Lower |
| Maximum Operating Pressure | | | | | | | | 50 PSI |
| Maximum Operating Flow Rate | | | | | | | | 60 LPM (Liter per Minute) |

Notes
1. Dimensions are in inches
2. Temperature is in ° centigrade

While the invention and process has been described with specific particularity to the drawings it should be understood that various changes and modifications may be made all without departing from the scope of the invention. For example while certain materials and modes of construction have been disclosed it should be obvious to those of ordinary skill in the art that various alternatives are available.

For example while a simple guide and screw stop has been disclosed with respect to positioning the platen 12 with associated lower manifold 60 at a certain vertical position relative to the upper manifold 18 it should be clear that a rack and pinion gear type arrangement is also feasible and indeed desirable where it is necessary to have more direct control over movement of the platen or table 12. Additionally, while some of the components have been shown as being of one piece construction it is obvious that multiple piece. construction will suffice as well. Moreover, instead of having the platen moveable, it could be rigid with the upper manifold being moveable with respect thereto, or both may be made moveable towards and away from each other.

Any and all such changes and modifications are intended to be covered by the appended claims.

While the present invention has been described with regards to particular embodiments, it is to be recognized that additional variations of the present invention may be devised without departing from the inventive concept.

What is claimed is:

1. An evaporator device comprising the combination of: a support stand comprising an upper span operatively supporting an upper gaseous fluid manifold forming an interior chamber for containing a gaseous fluid having an increased back pressure and having a plurality of gaseous fluid outlets for dispensing said gaseous fluid therefrom, said fluid outlets being in direct and open fluid communication with said interior chamber for passage of said gaseous fluid therethrough; a base member operatively secured to said upper horizontal span by at least one vertical support, said at least one vertical support operatively supporting a platen in moveable relationship with respect to said upper gaseous fluid manifold; and said platen being adapted to support a multiple compartment assay tray, having a substance in at least some of the compartments of said multiple compartment assay tray to be evaporated, for aligned and selected moveable relationship relative to said plurality of gaseous fluid outlets whereby gaseous fluid dispensed through said gaseous fluid outlets into at least some of said compartments of said assay tray evaporates said substance in said at least some of said compartment assay tray.

2. The device in accordance with claim 1 wherein said upper gaseous fluid manifold is adapted to be connected to a source of gaseous fluid and said upper gaseous fluid manifold comprises a plurality of hollow tubes forming gaseous fluid outlet passageways for gaseous fluid introduced into said upper gaseous fluid manifold.

3. The device in accordance with claim 2 wherein said plurality of hollow tubes is supported by a hollow tube support member which is releasably secured to said upper gaseous fluid manifold.

4. The device in accordance with claim 3 wherein said upper gaseous fluid manifold is formed by a compartment having upper and side walls and said hollow tube support member forms the lower wall thereof.

5. The device in accordance with claim 4 wherein a snap and hinge member is operatively secured to said upper gaseous fluid manifold and said hollow tube support member to maintain gaseous fluid tight connection there between.

6. The device in accordance with claim 4 wherein a thumb screw and friction engagement member allows for vertical positioning of said platen along a vertical path of travel defined by said at least one vertical support.

7. The device in accordance with claim 3 wherein said platen additionally includes a support surface for supporting said multiple compartment assay tray thereon.

8. The device in accordance with claim 7 wherein said platen includes a lower gaseous fluid manifold member having closed side and bottom walls with a removable top wall.

9. The device in accordance with claim 8 wherein said removable top wall supports a plurality of spaced, hollow tubes forming gaseous fluid pathway outlets from the interior of said lower gaseous fluid manifold member.

10. The device in accordance with claim 8 wherein said lower gaseous fluid manifold member is adapted to be connected to a source of gaseous fluid.

11. The device in accordance with claim 10 wherein said lower gaseous fluid manifold member is deep enough to receive said plurality of spaced, hollow tubes when said removable top wall is inverted.

12. The device in accordance with claim 11 wherein the surface of said removable top wall opposite the surface beyond which said hollow tubes project is recessed to retain an assay tray in releasable relationship therewith.

13. The device in accordance with claim 12 wherein said removable top wall forms a relatively gaseous fluid tight seal with respect to the remainder of said lower gaseous fluid manifold.

14. The device in accordance with claim 13 wherein said vertical support comprises a rod and which additionally includes a second spaced rod and said platen is provided with encircling guides relative to each of each of said rods in order to guide said platen along its vertical path of travel.

15. The device in accordance with claim 13 wherein said base member comprises a platform configured in rectangular plate form and is adapted to additionally support auxiliary, accompanying control and regulatory devices thereon.

16. The device in accordance with claim 15 wherein said platform has spaced feet on the undersurface thereof.

17. The device in accordance with claim 13 wherein said hollow tube support member and said removable top wall are capable of being subjected to sterilization to thereby sterilize the individual hollow tubes supported by each.

18. The device in accordance with claim 1 wherein said plurality of gaseous fluid outlets are formed in part by hollow, depending tubes.

19. The device in accordance with claim 18 wherein each of said tubes has a detachable and plastic disposable tip.

20. The device in accordance with claim 18 wherein said hollow, depending tubes are of metal and extend almost through the bottom wall of said upper gaseous fluid manifold.

21. The device in accordance with claim 20 wherein each of said hollow, depending tubes are provided with a heat insulating member.

22. The device in accordance with claim 21 wherein said heat insulating member comprises a conically shaped open ended member adapted to be frictionally retained on each of said hollow tubes.

23. The device in accordance with claim 22 wherein said bottom wall of said upper gaseous fluid manifold has a plurality of bores therethrough, connecting to the interior thereof and forming spaced and aligned rows with the lower most portion of each of said bores being of sufficient diameter to retain said hollow, depending tubes in friction-fit relationship therewith.

24. The device in accordance with claim 1 wherein said upper gaseous fluid manifold has a temperature sensing probe extending into the interior thereof adapted to be operatively connected to a thermal couple for determining the temperature therein.

25. The device in accordance with claim 24 including regulatory apparatus for delivering metered amounts of heated gaseous fluid into said upper gaseous manifold.

26. The device in accordance with claim 7 wherein said multiple compartment assay tray has contiguous side wall portions disallowing for the passage of gaseous fluid between each compartment.

27. The device in accordance with claim 7 wherein said multiple compartment assay tray has spaced compartments which compartments are circular in cross-section and a gaseous fluid passage way is formed between each.

28. The device in accordance with claim 9 wherein said multiple compartment assay tray has spaced compartments which compartments are circular in cross-section, and have gaseous fluid passageways formed therebetween into which said plurality of spaced, hollow tubes are disposed.

29. The device in accordance with claim 16 wherein said hollow tube support member and said removable top wall are of molded plastic.

30. The device in accordance with claim 5 wherein said upper gaseous fluid manifold is of molded plastic.

31. Apparatus for isolating solids from liquids by evaporating said liquid, said apparatus comprising:
an upper manifold forming an interior chamber for containing drying gas having an increased back pressure and for directing said drying gas through a plurality of ports into a multi-compartment assay tray containing said liquids, said fluid ports being in direct and open fluid communication with said interior chamber for passage of said drying gas therethrough; a platen for supporting said multi-compartment assay tray in variable positions with respect to said plurality of ports and means to vertically and selectively orient said platen in one of a plurality of positions relative to said plurality of ports and conduit means for supplying heated gas to said upper manifold, whereby heated drying gas is delivered to each of the compartments of said multi-compartment assay tray to evaporate liquids therefrom.

32. A process for recovering solids form liquids by evaporating said liquids comprising the steps of:
(a) placing said liquids in individual compartments;
(b) establishing a heated gas compartment for containing a heated gas having an increased back pressure;
(c) directing heated gas from said heated gas compartment into each of said individual compartments through individual ports in direct and open fluid communication with said gas compartment aligned with each of said individual compartments;
(d) varying the distance between the liquid surface in each of said individual compartments and said individual ports through which heated gas is directed;
(e) recovering solid residue from each of said individual compartments.

33. A laboratory evaporator device comprising the combination of:

a gaseous fluid manifold forming an interior chamber for containing a gaseous fluid having an increased back pressure and having a plurality of gaseous fluid outlets in direct and open fluid communication with said interior chamber and being adapted to be connected to a source of gaseous fluid; an assay support adapted to support an assay tray having a plurality of compartments about equal in number to said gaseous fluid outlets, one of said gaseous manifold said assay support being vertically and operatively moveable relative to the other whereby the distance between said plurality of fluid outlets and said assay tray is selectively variable.

34. An evaporator device comprising the combination of:

a support stand comprising an upper span operatively supporting an upper gaseous fluid manifold forming an interior chamber for containing a gaseous fluid having an increased back pressure and adapted to be connected to a source of said gaseous fluid and having a plurality of depending hollow tubes forming gaseous fluid outlets, said outlets in direct and open fluid communication with said interior chamber; a base member operatively secured to said upper horizontal span by a vertical support, said vertical support operatively supporting a table adapted to hold an assay tray thereon and being supported in moveable relationship with respect to said upper gaseous fluid manifold; said table being supported by spaced and opposed vertical rods secured to said base and having a thumb and bolt friction engagement therebetween to secure said table in one of a selected position along a vertical pathway; said gaseous fluid manifold having a modular member supporting said depending hollow tubes which is removable therefrom for ease of sterilization whereby an assay tray having a plurality of samples therein may be evaporated.

\* \* \* \* \*